US008048083B2

(12) United States Patent
Shadduck et al.

(10) Patent No.: US 8,048,083 B2
(45) Date of Patent: Nov. 1, 2011

(54) BONE TREATMENT SYSTEMS AND METHODS

(75) Inventors: John H. Shadduck, Tiburon, CA (US); Csaba Truckai, Saratoga, CA (US)

(73) Assignee: DFINE, Inc., San Jose, CA (US)

( * ) Notice: Subject to any disclaimer, the term of this patent is extended or adjusted under 35 U.S.C. 154(b) by 1009 days.

(21) Appl. No.: 11/267,950

(22) Filed: Nov. 4, 2005

(65) Prior Publication Data

US 2006/0264965 A1    Nov. 23, 2006

Related U.S. Application Data

(60) Provisional application No. 60/625,347, filed on Nov. 5, 2004, provisional application No. 60/626,701, filed on Nov. 10, 2004.

(51) Int. Cl.
*A61B 17/56* (2006.01)
*A61F 2/44* (2006.01)
(52) U.S. Cl. ............... 606/94; 623/17.11; 623/23.54
(58) Field of Classification Search .............. 606/92–94, 606/32, 86 R; 623/17.11, 17.12, 17.16, 23.54
See application file for complete search history.

(56) References Cited

U.S. PATENT DOCUMENTS

| 5,292,362 A | 3/1994 | Bass et al. |
| 5,334,626 A | 8/1994 | Lin |
| 5,360,450 A | 11/1994 | Giannini |
| 5,571,189 A | 11/1996 | Kuslich |
| 5,648,097 A | 7/1997 | Nuwayser |
| 5,665,122 A | 9/1997 | Kambin |
| 5,676,700 A | 10/1997 | Black et al. |
| 5,997,580 A | 12/1999 | Mastrorio et al. |
| 6,129,763 A | 10/2000 | Chauvin et al. |
| 6,171,312 B1 | 1/2001 | Beaty |
| 6,231,615 B1 | 5/2001 | Preissman |
| 6,235,043 B1 | 5/2001 | Reiley |

(Continued)

FOREIGN PATENT DOCUMENTS

WO    WO 02/87416    4/2002

(Continued)

OTHER PUBLICATIONS

Carrodeguas, et al., "Injectable Acrylic Bone Cements for Vertebroplasty with Improved Properties", Journal of Biomedical Materials Research, XP002312783, vol. 68, No. 1, Jan. 15, 2004, pp. 94-104.

(Continued)

*Primary Examiner* — Eduardo C Robert
*Assistant Examiner* — David Comstock
(74) *Attorney, Agent, or Firm* — Knobbe Martens Olson & Bear LLP (57) ABSTRACT

Methods and instruments for treating an osteoporotic vertebral body or for treating a vertebral compression fracture. An exemplary method includes introducing an open knit structure together with a bone cement into a bone wherein the knit structure extends substantially throughout the interior of the cement volume. In one aspect of the invention, the bone cement volumes cures with the filament structure reinforcing the cement. In another aspect of the invention, the open knit structure is configured to direct flows of bone cement to apply forces for reducing a vertebral compression fracture. In another aspect of the invention, the system provides bone cement flows that extend through the knit structure thus allowing the cement to fully interdigitate with the cancellous bone.

28 Claims, 5 Drawing Sheets

U.S. PATENT DOCUMENTS

| | | |
|---|---|---|
| 6,280,456 B1 | 8/2001 | Scribner |
| 6,309,420 B1 | 10/2001 | Preissman |
| 6,348,679 B1 | 2/2002 | Ryan et al. |
| 6,375,659 B1 | 4/2002 | Erbe et al. |
| 6,436,140 B1 | 8/2002 | Liu et al. |
| 6,436,143 B1 | 8/2002 | Ross et al. |
| 6,458,127 B1 | 10/2002 | Truckai |
| 6,458,375 B1 | 10/2002 | Gertzman et al. |
| 6,607,557 B1 | 8/2003 | Brosnahan et al. |
| 6,620,185 B1 * | 9/2003 | Harvie et al. ................. 606/232 |
| 6,649,888 B2 | 11/2003 | Ryan et al. |
| 6,740,093 B2 * | 5/2004 | Hochschuler et al. .......... 606/94 |
| 6,767,350 B1 | 7/2004 | Lob |
| 6,790,233 B2 | 9/2004 | Brodke et al. |
| 6,814,736 B2 | 11/2004 | Reiley |
| 6,835,206 B2 | 12/2004 | Jackson |
| 6,929,640 B1 | 8/2005 | Underwood |
| 6,955,691 B2 | 10/2005 | Chae et al. |
| 6,958,061 B2 | 10/2005 | Truckai |
| 6,979,352 B2 | 12/2005 | Reynolds |
| 6,985,061 B2 | 1/2006 | Hafskjold et al. |
| 7,014,658 B2 | 3/2006 | Ralph et al. |
| 7,044,954 B2 | 5/2006 | Reiley |
| 7,153,306 B2 | 12/2006 | Ralph et al. |
| 7,186,267 B2 | 3/2007 | Aston et al. |
| 7,189,263 B2 | 3/2007 | Erbe et al. |
| 7,226,481 B2 | 6/2007 | Kuslich |
| 7,258,700 B2 | 8/2007 | Lambrecht et al. |
| 7,318,823 B2 | 1/2008 | Sharps et al. |
| 7,357,798 B2 | 4/2008 | Sharps et al. |
| 7,399,739 B2 | 7/2008 | Shimp |
| 7,435,247 B2 | 10/2008 | Woloszko et al. |
| 7,559,932 B2 | 7/2009 | Truckai et al. |
| 7,621,952 B2 | 11/2009 | Truckai et al. |
| 7,678,116 B2 | 3/2010 | Truckai et al. |
| 7,682,378 B2 | 3/2010 | Truckai et al. |
| 2002/0026195 A1 | 2/2002 | Layne et al. |
| 2002/0032447 A1 | 3/2002 | Weikel et al. |
| 2002/0082608 A1 | 6/2002 | Reiley et al. |
| 2002/0099385 A1 | 7/2002 | Ralph et al. |
| 2002/0123750 A1 | 9/2002 | Eisermann et al. |
| 2002/0147497 A1 | 10/2002 | Belef et al. |
| 2002/0156483 A1 | 10/2002 | Voellmicke et al. |
| 2002/0161373 A1 | 10/2002 | Osorio et al. |
| 2002/0177866 A1 | 11/2002 | Weikel et al. |
| 2002/0183851 A1 * | 12/2002 | Spiegelberg et al. ...... 623/22.12 |
| 2003/0032733 A1 | 2/2003 | Fisher et al. |
| 2003/0055511 A1 | 3/2003 | Schryver et al. |
| 2003/0069326 A1 | 4/2003 | Stangel et al. |
| 2003/0130373 A1 | 7/2003 | Walz et al. |
| 2003/0130738 A1 | 7/2003 | Hovda et al. |
| 2003/0199980 A1 | 10/2003 | Siedler |
| 2003/0220648 A1 | 11/2003 | Osorio et al. |
| 2003/0233096 A1 | 12/2003 | Osorio et al. |
| 2004/0006347 A1 | 1/2004 | Sproul |
| 2004/0024410 A1 | 2/2004 | Olson, Jr. et al. |
| 2004/0092948 A1 | 5/2004 | Stevens et al. |
| 2004/0110285 A1 | 6/2004 | Lendlein et al. |
| 2004/0167561 A1 | 8/2004 | Boucher et al. |
| 2004/0172058 A1 | 9/2004 | Edwards et al. |
| 2004/0172132 A1 | 9/2004 | Ginn |
| 2004/0193171 A1 | 9/2004 | DiMauro et al. |
| 2004/0225296 A1 | 11/2004 | Reiss et al. |
| 2004/0228898 A1 | 11/2004 | Ross et al. |
| 2004/0267271 A9 | 12/2004 | Scribner et al. |
| 2005/0059979 A1 | 3/2005 | Yetkinler et al. |
| 2005/0209595 A1 | 9/2005 | Karmon |
| 2005/0222681 A1 | 10/2005 | Richley et al. |
| 2005/0245938 A1 | 11/2005 | Kochan |
| 2005/0251149 A1 | 11/2005 | Wenz |
| 2005/0261781 A1 * | 11/2005 | Sennett et al. ............. 623/23.54 |
| 2006/0052743 A1 | 3/2006 | Reynolds |
| 2006/0052794 A1 | 3/2006 | McGill et al. |
| 2006/0052873 A1 | 3/2006 | Buck et al. |
| 2006/0074433 A1 | 4/2006 | McGill et al. |
| 2006/0079905 A1 | 4/2006 | Beyar et al. |
| 2006/0085009 A1 | 4/2006 | Truckai et al. |
| 2006/0085081 A1 | 4/2006 | Shadduck et al. |
| 2006/0089715 A1 | 4/2006 | Truckai et al. |
| 2006/0100635 A1 | 5/2006 | Reiley et al. |
| 2006/0106459 A1 | 5/2006 | Truckai et al. |
| 2006/0106549 A1 | 5/2006 | Olsson |
| 2006/0122621 A1 | 6/2006 | Truckai et al. |
| 2006/0122622 A1 | 6/2006 | Truckai et al. |
| 2006/0122623 A1 | 6/2006 | Truckai et al. |
| 2006/0122624 A1 | 6/2006 | Truckai et al. |
| 2006/0122625 A1 | 6/2006 | Truckai et al. |
| 2006/0198865 A1 | 9/2006 | Freyman et al. |
| 2006/0229625 A1 | 10/2006 | Truckai et al. |
| 2006/0264967 A1 | 11/2006 | Ferreyro et al. |
| 2006/0265077 A1 | 11/2006 | Zwirkoski |
| 2007/0162043 A1 | 7/2007 | Truckai et al. |
| 2007/0225705 A1 | 9/2007 | Osorio et al. |
| 2007/0233146 A1 | 10/2007 | Henniges et al. |
| 2007/0233249 A1 | 10/2007 | Shadduck |
| 2007/0233250 A1 | 10/2007 | Shadduck |
| 2009/0275995 A1 | 11/2009 | Truckai et al. |

FOREIGN PATENT DOCUMENTS

| | | |
|---|---|---|
| WO | WO 2006/031490 | 9/2005 |

OTHER PUBLICATIONS

B. Heublein, R. Rohde, V. Kaese, M. Niemeyer, W. Hartung, A. Haverich, "Biocorrosion of magnesium alloys: a new principle in cardiovascular implant technology?", Heart, 2003; 89:651-656.

Office Action in U.S. Appl. No. 11/215,730, mailed Apr. 3, 2008.

Office Action in U.S. Appl. No. 11/215,730, mailed Jan. 23, 2009.

Carrodeguas et al., "Injectable Acrylic Bone Cements for Vertebroplasty with Improved Properties", *Journal of Biomedical Materials Research*, XP002312783, vol. 68, No. 1, Jan. 15, 2004, pp. 94-104.

B. Heublein et al. "Biocorrosion of magnesium alloys: a new principle in cardiovascular implant technology?", Heart 2003: 89:651-656.

International Search Report, mailing date Jun. 20, 2006, PCT/US2005/043984, 3 pg.

International Search Report, mailing date May 31, 2006, PCT/US2005/044055, 4 pg.

Office Action dated Nov. 1, 2007 received in U.S. Appl. No. 11/199,582.

Office Action dated Jan. 10, 2008 received in U.S. Appl. No. 11/146,891.

Office Action dated Feb. 28, 2008, received in U.S. Appl. No. 11/146,893.

Office Action dated Mar. 28, 2008 received in U.S. Appl. No. 11/267,950.

Office Action dated Apr. 3, 2008 received in U.S. Appl. No. 11/215,730.

U.S. Appl. No. 12/624,086, filed Nov. 23, 2009, Truckai et al.

* cited by examiner

BONE TREATMENT SYSTEMS AND METHODS

CROSS-REFERENCE TO RELATED APPLICATIONS

This application claims benefit of Provisional U.S. Patent Application Ser. No. 60/625,347 filed Nov. 5, 2004 titled Systems and Methods for Treating Vertebral Fractures and also claims benefit of Provisional U.S. Patent Application Ser. No. 60/626,701 filed Nov. 10, 2004 titled Systems and Methods for Treating Vertebral Fractures. This application also is related to U.S. application Ser. No. 11/165,652 filed Jun. 24, 2005 titled Bone Treatment Systems and Methods; and U.S. patent application Ser. No. 11/165,651 filed Jun. 24, 2005, titled Bone Treatment Systems and Methods. The entire contents of all of the above cross-referenced applications are hereby incorporated by reference in their entirety and should be considered a part of this specification.

BACKGROUND OF THE INVENTION

1. Field of the Invention

The present invention relates to medical devices, and more particularly to methods and apparatus for introducing fill material into a bone and for applying retraction forces to bone. An exemplary embodiment is used for applying forces to reduce a vertebral fracture.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the affected population will grow steadily as life expectancy increases. Osteoporosis affects the entire skeleton but most commonly causes fractures in the spine and hip. Spinal or vertebral fractures also have serious consequences, with patients suffering from loss of height, deformity and persistent pain which can significantly impair mobility and quality of life. Fracture pain usually lasts 4 to 6 weeks, with intense pain at the fracture site. Chronic pain often occurs when one level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporotic bone, the sponge-like cancellous bone has pores or voids that increase in dimension, making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. In one percutaneous vertebroplasty technique, bone cement such as PMMA (polymethylmethacrylate) is percutaneously injected into a fractured vertebral body via a trocar and cannula system. The targeted vertebrae are identified under fluoroscopy. A needle is introduced into the vertebral body under fluoroscopic control to allow direct visualization. A transpedicular (through the pedicle of the vertebrae) approach is typically bilateral but can be done unilaterally. The bilateral transpedicular approach is typically used because inadequate PMMA infill is achieved with a unilateral approach.

In a bilateral approach, approximately 1 to 4 ml of PMMA are injected on each side of the vertebra. Since the PMMA needs to be forced into cancellous bone, the technique requires high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique—and the physician terminates PMMA injection when leakage is evident. The cement is injected using small syringe-like injectors to allow the physician to manually control the injection pressures.

Kyphoplasty is a modification of percutaneous vertebroplasty. Kyphoplasty involves a preliminary step that comprises the percutaneous placement of an inflatable balloon tamp in the vertebral body. Inflation of the balloon creates a cavity in the bone prior to cement injection. Further, the proponents of percutaneous kyphoplasty have suggested that high pressure balloon-tamp inflation can at least partially restore vertebral body height. In kyphoplasty, it has been proposed that PMMA can be injected at lower pressures into the collapsed vertebra since a cavity exists to receive the cement—which is not the case in conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles. Leakage of PMMA during vertebroplasty can result in very serious complications including compression of adjacent structures that necessitate emergency decompressive surgery.

Leakage or extravasation of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al, "The Analysis of Polymethylmethacrylate Leakage after Vertebroplasty for Vertebral Body Compression Fractures", Jour. of Korean Neurosurg. Soc. Vol. 35, No. 5 (May 2004) pp. 478-82, (http://www.jkns.or.kr/htm/abstract.asp?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol. 2004 February; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al., "Asymptomatic diffuse pulmonary embolism caused by acrylic cement: an unusual complication of percutaneous vertebroplasty", Ann. Rheum. Dis. 2003; 62:85-86. The vapors from PMMA preparation and injection are also cause for concern. See Kirby, B., et al., "Acute bronchospasm due to exposure to polymethylmethacrylate vapors during percutaneous vertebroplasty", Am. J. Roentgenol. 2003; 180:543-544.

Another disadvantage of PMMA is its inability to undergo remodeling—and the inability to use the PMMA to deliver osteoinductive agents, growth factors, chemotherapeutic agents and the like. Yet another disadvantage of PMMA is the need to add radiopaque agents which lower its viscosity with unclear consequences on its long-term endurance.

In both higher pressure cement injection (vertebroplasty) and balloon-tamped cementing procedures (kyphoplasty), the methods do not provide for well controlled augmentation of vertebral body height. The direct injection of bone cement simply follows the path of least resistance within the fractured bone. The expansion of a balloon also applies compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to 200 or 300 psi) to inflate the balloon which first crushes and compacts cancellous bone. Expansion of the balloon under high pressures close to cortical bone can fracture the cortical bone, or cause regional damage to the cortical bone that can result in cortical bone necrosis. Such cortical bone damage is highly undesirable and results in weakened cortical endplates.

Kyphoplasty also does not provide a distraction mechanism capable of 100% vertebral height restoration. Further, the kyphoplasty balloons under very high pressure typically apply forces to vertebral endplates within a central region of the cortical bone that may be weak, rather than distributing forces over the endplate.

There is a general need to provide systems and methods for use in treatment of vertebral compression fractures that provide a greater degree of control over introduction of bone support material, and that provide better outcomes. Embodiments of the present invention meet one or more of the above needs, or other needs, and provide several other advantages in a novel and non-obvious manner.

SUMMARY OF THE INVENTION

The invention provides implant systems and methods for treatment of vertebral compression fractures, as well as systems for prophylactic treatment of osteoporotic vertebrae in patients that are susceptible to compression fractures. The invention also can be used in correcting and supporting bones in other abnormalities such as bone tumors and cysts, avascular necrosis of the femoral head and tibial plateau fractures.

In one embodiment, an apparatus and method of the invention includes introducing an open web, technical knit structure together with a flow of PMMA bone cement into a targeted site in bone such as a vertebra. In one aspect of the invention, the knit structure will extend continuously throughout the interior of the volume of bone cement to provide reinforcing for the cured cement. In another aspect of the invention, the web openings of the knit structure are configured to allow cement flows therethrough, but the web opening dimensions have a selected non-uniform configuration to direct flows and fluid pressures of the inflowing cement to apply forces in a controlled direction for reducing a vertebral compression fracture. In any embodiment, the bone cement flows through the knit structure thus allowing cement interdigitation with the cancellous bone.

In another embodiment of the invention, the apparatus includes a technical knit structure that is coupled to an energy source to thereby heat the inflowing bone cement to controllably change the viscosity of the cement. In one embodiment, the knit structure has at least one portion that is fabricated of a conductive filament and is coupled to a radiofrequency source and controller. The knit structure then can be operated in a bi-polar or mono-polar manner to controllable heat the inflowing bone cement or a selected portion thereof.

These and other objects of the present invention will become readily apparent upon further review of the following drawings and specification.

There is a general need to provide systems and methods for use in treatment of vertebral compression fractures that provide a greater degree of control over introduction of bone support material, and that provide better outcomes. The present invention meets this need and provides several other advantages in a novel and nonobvious manner.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE INVENTION

Figure 1:
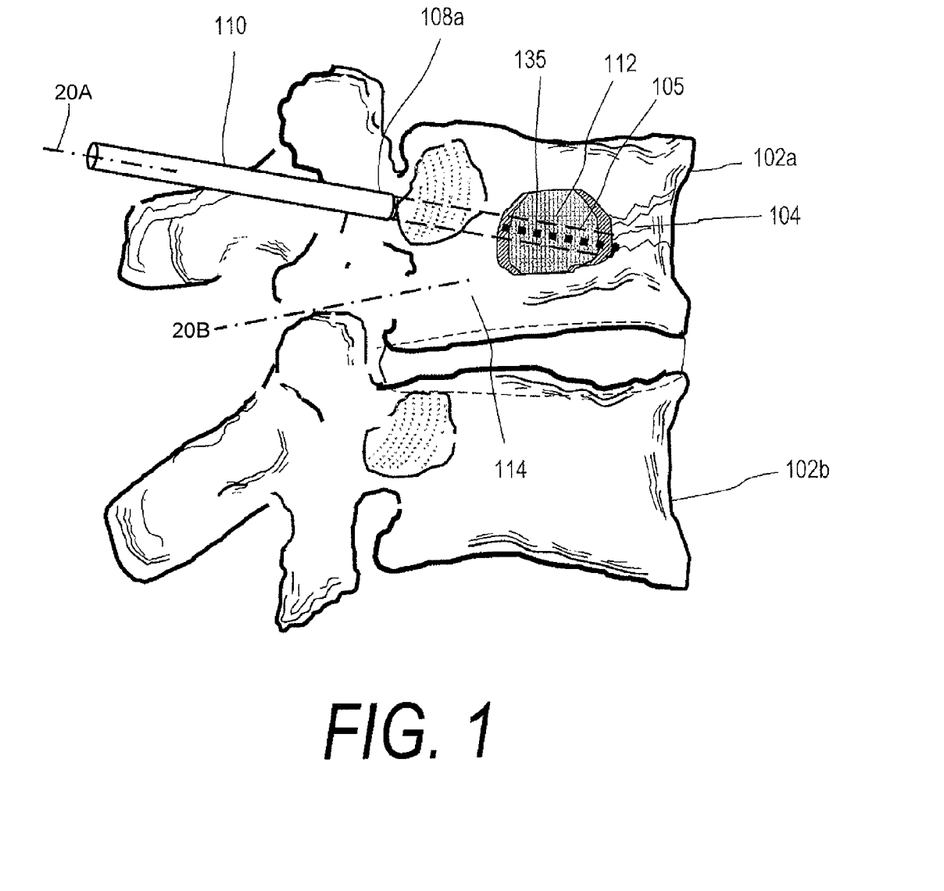
FIG. 1 is a view of a spine segment with one vertebra having a vertebral compression fracture (VCF).

In FIG. 1, it can be seen that vertebral body 102a has a wedge vertebral compression fracture (VCF) indicated at 104 and the methods of the invention are directed to safely introducing a bone cement into cancellous bone to eliminate pain and to reduce the fracture. Vertebral body 102b is susceptible to a VCF following treatment of the fractured vertebra 102a since biomechanical loading will be altered. The present invention includes systems for prophylactically treating a vertebra that is adjacent to vertebral compression fracture, as well as for the treating the fractured vertebra.

Figure 2:
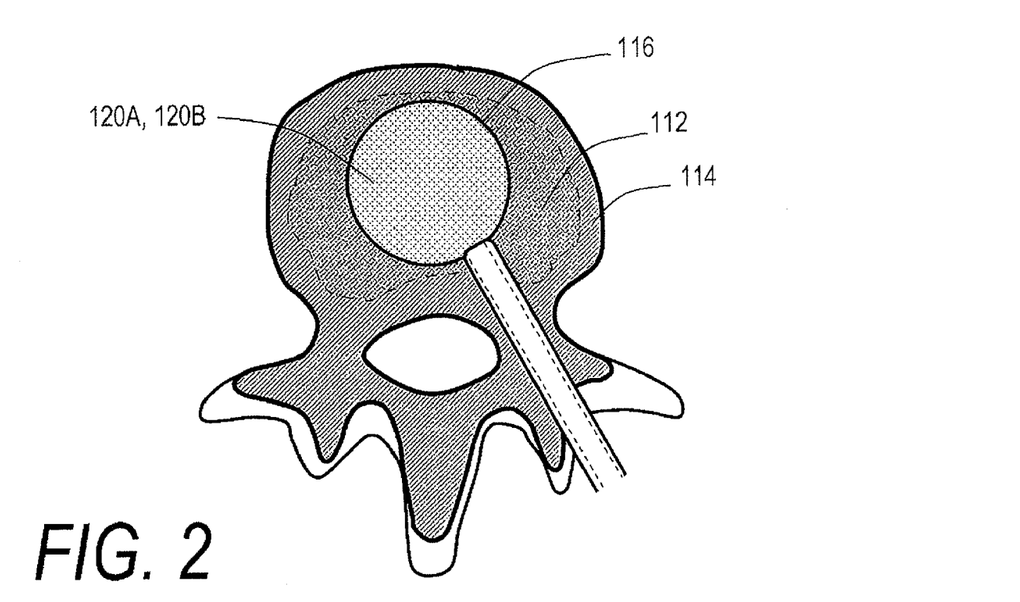
FIG. 2 is a sectional view of a vertebra with an introducer treating a VCF in a single posterior access.
Figure 3:
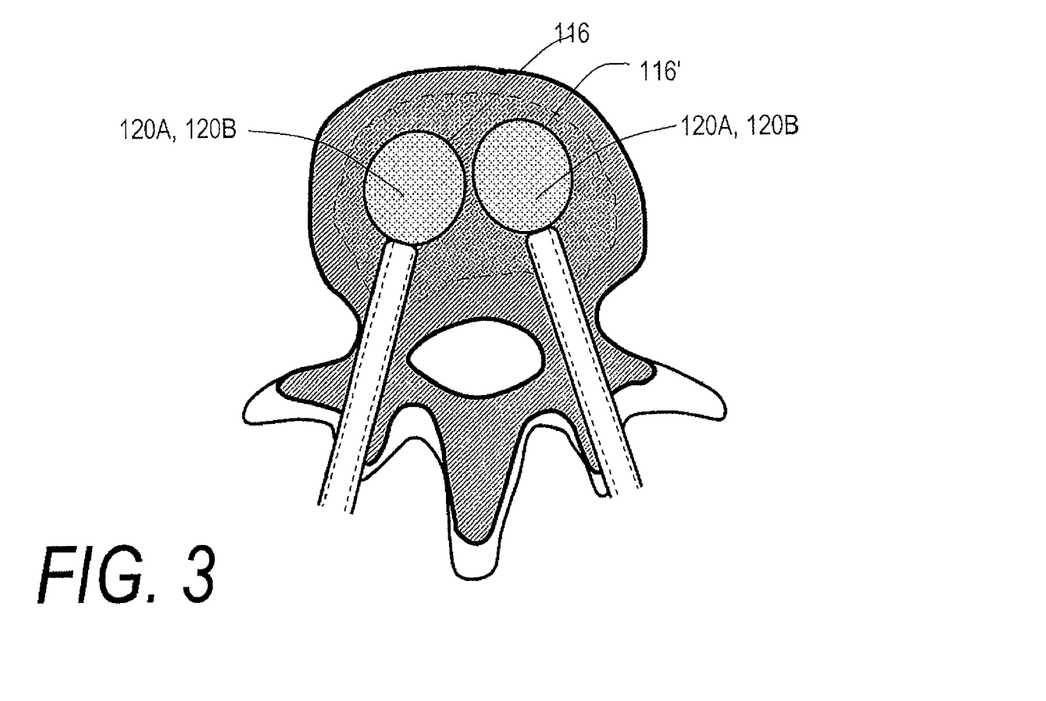
FIG. 3 is a sectional view of a vertebra with introducers treating a VCF in a bilateral transpedicular approach.

FIG. 1 illustrates an initial step of a method of the invention wherein the distal working end 105 of an elongate introducer 110 is introduced through the saddle of pedicle 108a for penetration along axis 20A into the osteoporotic cancellous bone 112. It should be appreciated that the instrument also can be introduced into the vertebra in an extrapedicular approach, for example, through the cortical wall 114 of the vertebra as indicated along axis 20B in FIG. 1. FIG. 2 illustrates a plan shape 116 of an exemplary volume of infill material in a treatment region of a vertebra that comprises an open knit structure 120A and a bone cement component 120B described in more detail below. The knit structure 120A is configured for reinforcing a volume of bone cement as well as for directing the flow of cement to apply forces to elevate height of the fractured vertebra. FIG. 3 is another sectional view of a vertebra showing that bipedicular accesses and two targeted treatment regions 116 and 116' in a variation of the treatment method. As will be described below, the introducer can include a detachment mechanism indicated at 118 for releasing the knit filament reinforcing structure 120A from the introducer after deployment in the vertebra.

Figure 4A:
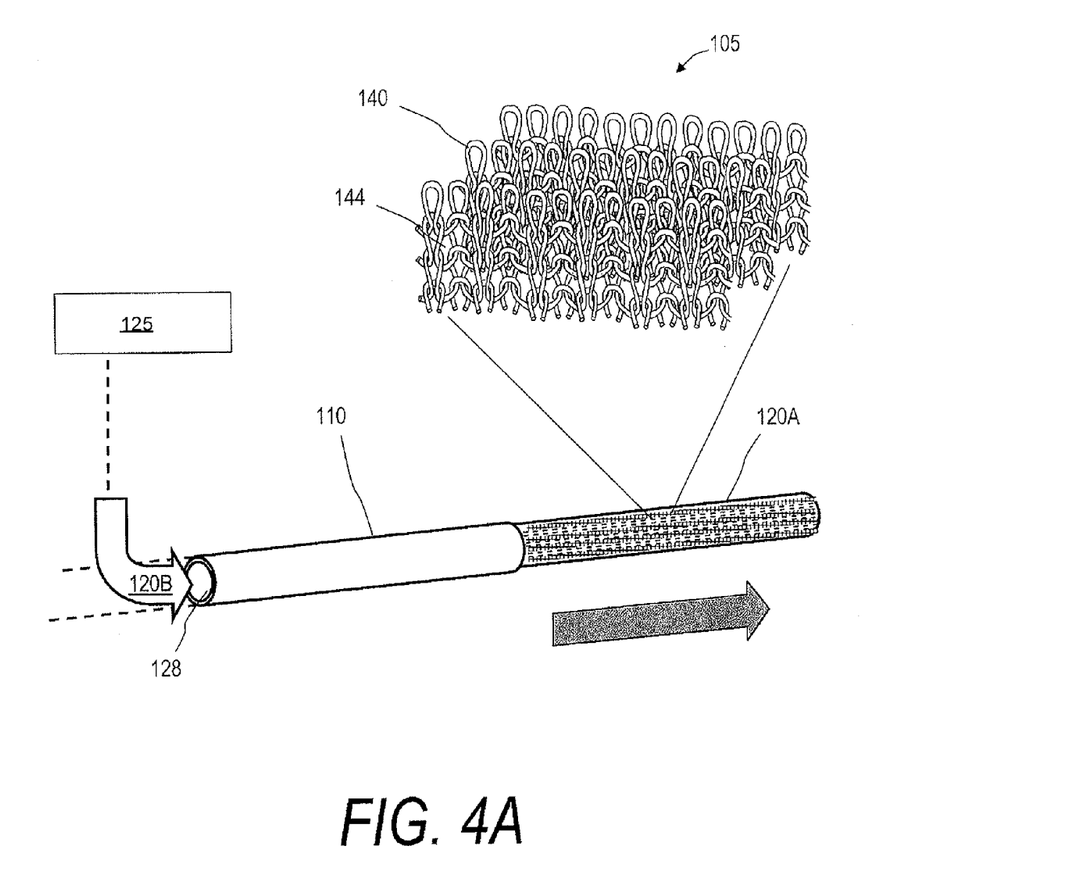
FIG. 4A is a schematic view of an introducer working end of the invention that carries an open knit structure for reinforcing a volume of bone cement and for directing flow of a bone cement, the knit structure in a reduced cross sectional configuration.
Figure 4B:
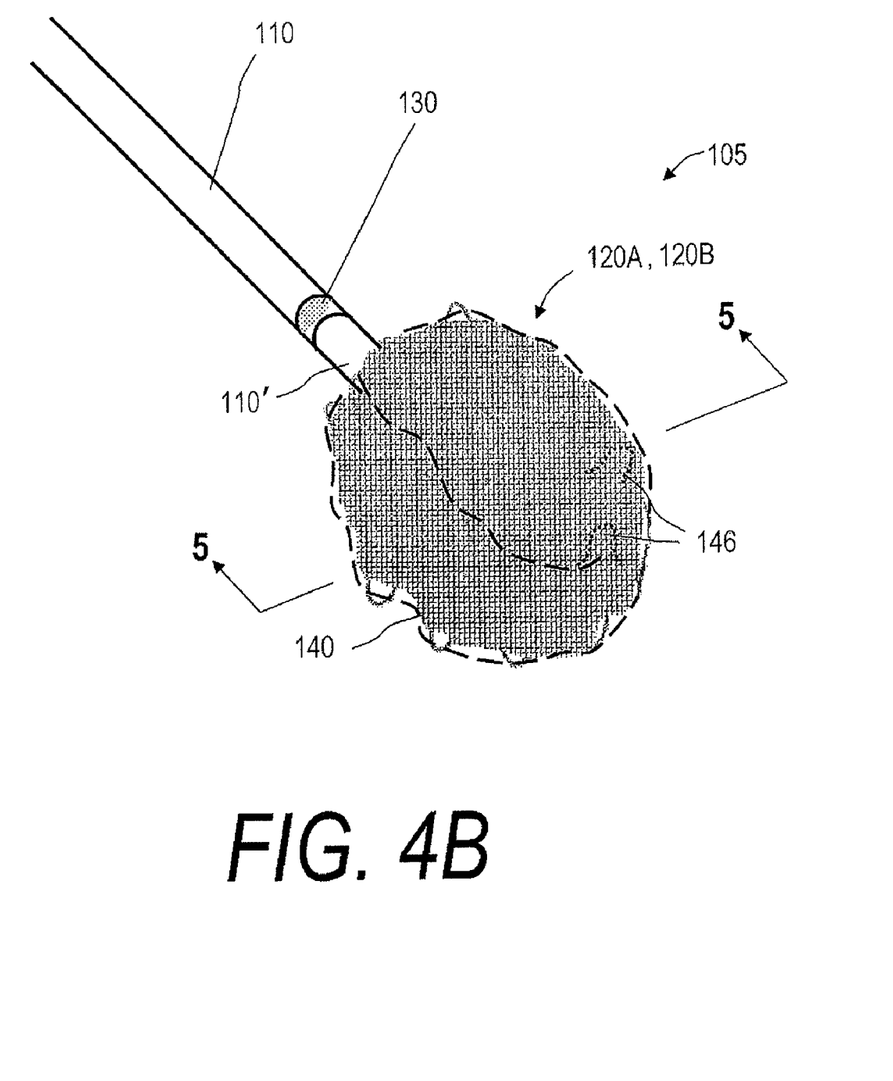
FIG. 4B is a schematic view of a working end similar to that of FIG. 4A, with the open knit structure having cement flowing therethrough which moves the knit structure to an extended condition.

FIGS. 4A and 4B illustrate a bone fill system comprising working end 105 that includes an exemplary open knit reinforcing structure (a first component) 120A and a bone cement (second a component) 120B which is injected from pressurized cement source 125 coupled to the channel in introducer 110 as is known in the art. The second component or bone cement 120A can be a PMMA as is known in the art of vertebroplasty or the cement can be any other in-situ hardenable composition, for example a monocalcium phosphate, tricalcium phosphate, calcium carbonate, calcium sulphate or hydroxyapatite.

FIG. 4A illustrates the introducer 110 with technical knit structure 120A in a pre-deployed, compacted condition. The open knit structure 120A can be slidably introduced into bone from bore 128 of the introducer 110 as depicted in FIG. 4A. In one embodiment, the cement 120B can be delivered into the interior of such a deployable knit structure 120A by a flexible tube that can be cut or detached from the knit structure. In another embodiment as shown in FIG. 4B, the knit structure 120A is detachable from the introducer 110 by a detachment mechanism 130 as will be described below wherein a distal portion 110' of the introducer and knit structure 120A are de-coupled from a proximal portion of the introducer. FIG. 4B further depicts that knit structure 120A can move toward an extended condition as cement is flowed into and through the structure wherein the knit structure functions to reinforce the volume of cement by extending throughout the cement. Further, the knit structure 120A is configured for directing flows of cement by providing knit filaments 140 with non-uniform web openings 144 in the web of filaments. As can be seen in FIG. 4B, the open knit structure 120A will increase in cross-section with the flow of bone cement 120B therein which can result in any shape as exemplary portions 146 of will interdigitate into cancellous bone along with the knit structure.

Of particular interest, the first and second components 120A and 120B when combined as a composite (i) can provide an implant structure that allows for interdigitation of bone cement into cancellous bone for stabilizing micromotion to eliminate pain, (i) can provide reinforcement for the injected bone cement volume 120B to resist compression loads without fracturing even if in a thin cross-section, (iii) can be provided with non-uniform web openings 144 to direct flow of cement preferentially toward larger opening and away from smaller openings to direct forces for reducing a fracture, and (iv) can optionally provide an at least partly resorbable knit filaments to allow for eventual bone ingrowth into and throughout the cement layer or monolith.

Of particular interest, the open technical knit structure or first component 120A provides means for controlling the vectors of distraction forces caused by inflows of second component 120B (bone cement) within the first component 120A in the process of injecting and deploying the media in vertebral cancellous bone. In one aspect of the invention, the open technical knit 120A allows for the injection of bone cement to preferentially create forces that are focused for the fracture of horizontal plane 135 (FIG. 1) in cancellous bone. In another aspect of the invention, the open knit structure 120A preferentially create forces that are distributed over a broad surface area to reduce a fracture and at least partly restore vertebral height.

Figure 5:
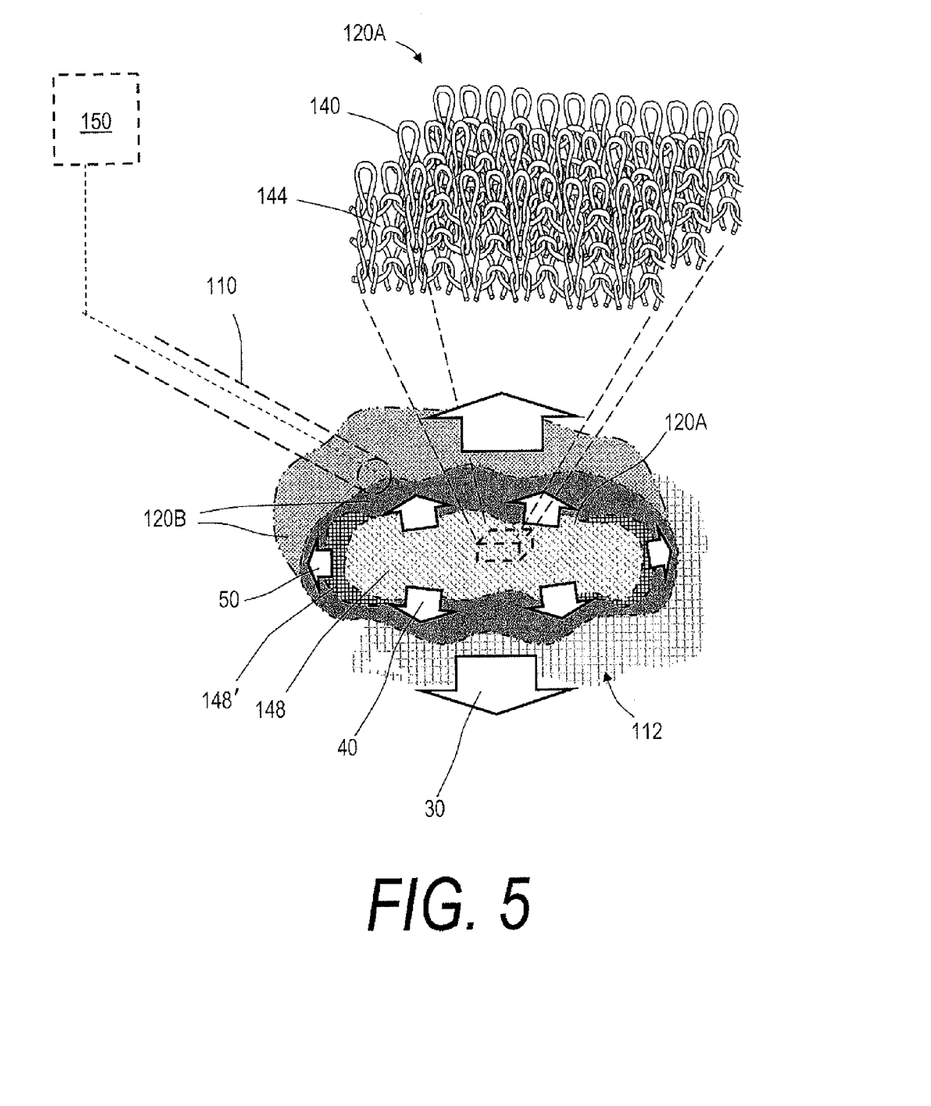
FIG. 5 is a cross sectional view of a volume of bone cement and the open knit structure of FIGS. 4A and 4B illustrating the system directing flows of the bone cement and the application of forces by the re-directed fluid pressure.

Referring to FIG. 5, it can be seen that the open knit structure 120A in cross-section allows cement to flow therethrough and into cancellous bone 112. Thus, the system allows for cement interdigitation into the cancellous bone which it is believed will optimally prevent micromotion which results from the VCF. Such micromotion in an acute VCF is believed to be principal source of vertebral body pain. In FIG. 5, it also can be seen that the open knit structure 120A comprises strands or filaments 140 that are looped or stitched and extend throughout the interior of the structure 120A to create a continuous three dimensional reinforcing network within the interior of volume of cement 120B. The technical knit 120A is preferably a titanium, stainless steel, tungsten or NiTi wire, but can also be any suitable polymer, carbon fiber, glass fiber and further includes biodegradable polymer filaments and metal filaments such as magnesium alloys. Technical knitting machines for medical device manufacturing are available from Stoll GmbH & Co. KG, Stollweg 1, 72760 Reutlingen, Germany.

In one embodiment as depicted in FIG. 5, the technical knit 125 defines an open gradient therein that is defined as a gradient or change in the mean dimension of web openings 144 between filaments 140 that allow the migration of a composite cement, wherein the cement 120B is a viscous PMMA or an cement that includes a filler of a granular material. In FIG. 5, the sectional view of the knit structure illustrates that the gradient extends to smaller mean open dimensions toward the lateral surfaces, with greater dimensioned open web configurations 148 in the central region and central surfaces and lesser dimensioned open webs 148' in the lateral portions. The scope of the invention includes any number of different regions of the knit structure 120A having different web opening dimensions. It can be easily understood that the direction of pressurized flows of cement 120B into and through knit structure 120A will be re-directed by the predetermined open web configuration—and thereby the vectors of forces can be controlled to a selected extent by the open knit reinforcing filaments 140 and its open web orientation. In FIG. 5, it can be seen that fluid pressures are maximized (see arrows) for reducing a fracture. Arrows 30 represent the fluid pressure and arrows 40 and 50 respectively represent the greater and lesser flows of bone cement. Thus, a method corresponding to the invention controls the vectors of distraction forces against bone using pressurized media flows, wherein a first step includes delivering into an interior region of a patient's body a deformable open web filamentous knit structure that defines selected dimension web openings between the filament, and causing pressurized flows of a cement in a first direction into the structure wherein the viscosity of the cement will preferentially self-select flow paths in a modified direction of least resistance through the larger dimensioned open webs to thereby direct distraction forces in the selected direction. In another similar method, the cement 120B can carry optional granular fillers wherein the fillers will aggregate in predetermined openings in the open-strand structure to obstruct inflows in a first direction to thereby direct inflows and distraction forces in a second direction.

In another embodiment similar to FIG. 4A, a knit structure 120A can be crushed into a cylindrical shape for introduction into cancellous bone wherein the structure has a non-extended configuration with a diameter similar to that of the introducer which can be from about 2.5 to 5 mm. In one embodiment, the knit structure 120A is maintained in a cylindrical-like shape by means of a biocompatible fracturable media that encases the knit structure 120A, such as a thin layer of a fracturable polymer (e.g., PMMA or any bioabsorbable polymer) in which the structure is coated. In another embodiment, the knit structure 120A similar to FIG. 4A is constrained within a thin break-away constraining sleeve that has a weakened line for bursting upon pressurized inflows therein to move toward the structure toward an extended configuration as in FIGS. 4 and 5.

In any embodiment, the flows of cement optionally can be pulsed at from 1 Hz to 1000 Hz, or preferably from 10 to 100 Hz, to provide enhanced flow characteristics for interdigitation in cancellous bone and for enhancing cement flows through the knit structure 120A. In a related method of the invention, the cement component 120B can be introduced into the knit structure 120A in different volumes wherein each volume differs in the dimension or percentage of granular materials therein to control the aggregation of such materials in open webs 144 of the knit structure 125. The infill materials can be porous scaffold materials and can include thermally insulative solid or hollow microspheres of a glass or other material for reducing heat transfer to bone from the exothermic reaction in a typical bone cement.

In preferred embodiments, the knit reinforcing construct 120A is fabricated by technical knitting of strands, wires, filaments or the like. The fabrication also can include entangled strands as in steel wool-like or cotton ball-like materials, or woven strands or braided strands which all fall within the scope of the invention. Technical knitting machines are preferred since the machines have the ability to fabricate open strand materials that have controlled gradients in thick materials and in three dimensions. In another embodiment, an open web structure can comprise an open cell foam wherein the strands can be alternatively defined as the ligaments that surround open cells, as generally disclosed in co-pending Provisional U.S. Patent Application Ser. No. 60/605,700 filed Aug. 30, 2004 titled Vertebral Implant Constructs, Methods of Use and Methods of Fabrication, which is incorporated herein in its entirety by this reference. In other embodiments of open web filamentous structures, the structure can be provided by a fabrication process selected from the group of knitting filaments, weaving filaments, braiding filaments and entangling filaments.

In another embodiment, the knit structure 120A is fabricated of a electrically conductive metal filament and is optionally connected to an electrical energy source 150 as depicted in FIG. 5. The filaments can be resistively heated or function as at least one electrode to thereby heat the cement to increase its viscosity as more generally disclosed in co-pending U.S. application Ser. No. 11/165,652 filed Jun. 24, 2005 titled Bone Treatment Systems and Methods and U.S. patent application Ser. No. 11/165,651 filed Jun. 24, 2005, titled Bone Treatment Systems and Methods. In one such embodiment, a knit structure 120A can include a plurality of spaced apart conductive filament portions separated by non-conductive filament portions with the conductive filament portions functioning as opposing polarity electrodes to thereby operate in a bi-polar manner. In other embodiments, a knit structure 120A can function in a mono-polar manner in conjunction with a ground pad. The scope of the invention includes using any type of energy absorbing or energy transmitting filaments that cooperate with an energy source for heating and altering the viscosity of the bone cement. The energy source coupled to the knit structure 120A can comprise an ultrasound energy source, a radiofrequency energy source, a resistive heating source, a light energy or laser source, a microwave energy source, or an inductive heating source. The scope of the invention extends to using any such energy absorbing or energy transmitting elements of filaments that are introduced with a bone cement, whether the elements are knit, entangled or simply unassembled elongated filaments that flow with the bone cement for heating the bone cement.

In another embodiment, a knit structure 120A similar to that of FIG. 4A can be introduced together with bone cement 120B into a plurality of cut or drilled paths in a vertebral body not having a compression fracture for the purpose of reinforcing the vertebra as disclosed in the authors' Provisional U.S. Patent Application Ser. No. 60/622,209 filed Oct. 26, 2004 titled Systems and Methods for Treating Vertebral Fractures, which is incorporated herein in it entirety by this reference and made a part of this specification.

Referring to FIG. 4B, the release mechanism 130 or detachment structure can be any suitable mechanism such as a screw thread, a releasable clamp, a thermally sacrificial polymer, a fracturable element or a scored frangible structure that is broken by extension forces. One example known in the art is NiTi actuated frangibolt system that was developed for reliable satellite deployment in space. The invention encompasses the uses of a NiTi actuator to separate an implantable medical device working end from an introducer or catheter and is described in more detail in co-pending U.S. application Ser. No. 11/165,652 filed Jun. 24, 2005 titled Bone Treatment Systems and Methods.

The above description of the invention intended to be illustrative and not exhaustive. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed:

1. A system for reducing a vertebral fracture, comprising:
 a knit structure comprising a plurality of filaments, the knit structure configured for expandable extension within the interior of an injected volume of bone cement;

an introducer for introducing the knit structure and bone cement into a vertebra; and an electrical or electromagnetic energy source configured to couple to the knit structure such that at least a portion of the plurality of filaments is electrically coupled to the electrical or electromagnetic energy source to apply energy from the electrical or electromagnetic energy source to the volume of bone cement.

2. The system for reducing a vertebral fracture of claim 1 wherein the knit structure has non-uniform openings between filaments of the knit structure.

3. The system for reducing a vertebral fracture of claim 2 wherein the filaments are metal.

4. The system for reducing a vertebral fracture of claim 2 wherein the filaments are at least one of titanium, stainless steel and tungsten.

5. The system for reducing a vertebral fracture of claim 2 wherein the filaments are at least partly of a polymer.

6. The system for reducing a vertebral fracture of claim 2 wherein the filaments are at least partly of a conductive polymer.

7. The system for reducing a vertebral fracture of claim 1 wherein the electrical or electromagnetic energy source coupled to the knit structure is selected from the group of electrical radiofrequency energy sources, resistive heating sources, ultrasound energy sources, microwave energy sources and inductive heating sources.

8. The system for reducing a vertebral fracture of claim 1 wherein the knit structure comprises at least one of knitted filaments, braided filaments, woven filaments and entangled filaments.

9. The system of claim 1, wherein the filaments comprise at least one electrode and wherein the energy source is configured to apply electrical energy to the at least one electrode to thereby apply energy to the bone cement and increase the viscosity of the bone cement.

10. The system of claim 1, wherein the filaments comprise resistively heated filaments.

11. The system of claim 1, wherein at least a portion of the plurality of filaments are resorbable.

12. The system of claim 1, wherein the filaments comprise a plurality of spaced apart conductive filaments separated by a plurality of non-conductive filaments wherein the plurality of conductive filaments are configured to function as opposing polarity electrodes to thereby act in a bipolar manner.

13. A system for treating a bone, comprising:
an open knit structure at least partly of conductive filaments configured for extension in cross section by the flow of bone cement therethrough; and
an electrical radiofrequency source coupled to the conductive filaments of the open knit structure and configured to apply electrical energy to the conductive filaments and thereby to apply energy to the bone cement.

14. The system of claim 13, wherein the open knit structure is coupled to a first pole of the radio frequency source.

15. The system of claim 13, wherein first and second portions of the open knit structure are coupled to respective first and second poles of the radio frequency source.

16. The system of claim 15, wherein said first and second portions of the open knit structure are of conductive filaments.

17. The system of claim 15, wherein said first and second portions of the open knit structure are coupled by an intermediate portion of non-conductive filaments.

18. A system comprising:
a knit structure configured to reinforce a volume of bone cement, wherein the knit structure extends substantially uniformly across a cross-section of the volume of bone cement, the knit structure comprising a plurality of filaments joined by technical knitting and forming a plurality of openings throughout the knit structure, wherein the bone cement is configured to flow into and through the openings; and
an electrical or electromagnetic energy source coupled to the knit structure and configured to apply electrical or electromagnetic energy to at least some of the plurality of filaments of the knit structure to thereby apply energy to the bone cement;
wherein the size of the openings forms a gradient that extends from the openings at a central region of the knit structure to openings at lateral surfaces, with smaller mean opening dimensions at the lateral surfaces, and greater mean opening dimensions in the central region and in a top and bottom central surface.

19. The system of claim 18, wherein the energy source comprises at least one of an electrical radiofrequency energy source, a resistive heating source, a light energy source, an ultrasound energy source, a microwave energy source and an inductive heating source.

20. The system of claim 18, wherein the filaments are at least partly of a conductive polymer or a metal.

21. The system of claim 19, wherein the at least a portion of the plurality of filaments comprise resistively heated filaments.

22. The system of claim 19, wherein the plurality of filaments comprise a plurality of spaced apart conductive filaments separated by a plurality of non-conductive filaments.

23. The system of claim 19, wherein the filaments comprise at least one electrode.

24. A system for reducing a vertebral fracture, comprising:
a knit structure comprising a plurality of spaced apart conductive filaments separated by a plurality of non-conductive filaments, wherein the knit structure is configured for expandable extension substantially throughout the interior of an injected volume of bone cement; and
an electrical energy source configured to couple to the knit structure such that the plurality of conductive filaments are electrically coupled to the electrical energy source;
wherein the plurality of conductive filaments are configured to function as opposing polarity electrodes to thereby act in a bipolar manner to apply energy from the electrical energy source to the volume of bone cement.

25. The system of claim 24, wherein the knit structure has non-uniform openings between filaments of the knit structure.

26. The system of claim 24, wherein the knit structure is configured to comprise a continuous three dimensional reinforcing network within the interior of the injected volume of bone cement.

27. The system of claim 24, wherein the knit structure comprises at least one of knitted filaments, braided filaments, woven filaments and entangled filaments.

28. The system of claim 24, wherein the electrical energy source comprises an electrical radiofrequency energy source.

* * * * *